US006855499B1

(12) United States Patent
Nargessi

(10) Patent No.: US 6,855,499 B1
(45) Date of Patent: Feb. 15, 2005

(54) MAGNETIC ISOLATION AND PURIFICATION OF NUCLEIC ACIDS

(75) Inventor: Ruhangiz D. Nargessi, Alameda, CA (US)

(73) Assignee: Cortex Biochem, Inc., San Leandro, CA (US)

( * ) Notice: Subject to any disclaimer, the term of this patent is extended or adjusted under 35 U.S.C. 154(b) by 482 days.

(21) Appl. No.: 09/972,752

(22) Filed: Oct. 5, 2001

Related U.S. Application Data

(60) Provisional application No. 60/269,729, filed on Feb. 16, 2001.

(51) Int. Cl.[7] .......................... C12Q 1/68; C12P 19/34; C12M 1/34; C07H 21/02; C07H 21/04
(52) U.S. Cl. .......................... 435/6; 435/7.1; 435/91.1; 435/91.2; 435/287.2; 530/22.1; 530/23.1; 530/24.3; 530/24.31; 530/24.32; 530/24.33
(58) Field of Search .......................... 435/6, 7.1, 91.1, 435/91.2, 287.2; 536/22.1, 23.1, 24.3–24.33

(56) References Cited

U.S. PATENT DOCUMENTS

| | | | |
|---|---|---|---|
| 4,921,805 A | 5/1990 | Gebeyehu et al. | |
| 5,234,809 A | 8/1993 | Boom et al. | |
| 5,437,983 A | 8/1995 | Watts et al. | |
| 5,564,104 A | 10/1996 | Pourfarzaneh | |
| 5,705,628 A | 1/1998 | Hawkins | |
| 5,790,964 A | 8/1998 | Pourfarzaneh | |
| 5,898,071 A | 4/1999 | Hawkins | |
| 6,027,945 A | 2/2000 | Smith et al. | |
| 6,103,127 A | 8/2000 | Pourfarzaneh | |
| 6,416,671 B1 | 7/2002 | Pourfarzaneh | |

FOREIGN PATENT DOCUMENTS

| | | |
|---|---|---|
| WO | 91-12079 WO | 8/1991 |
| WO | 02-066993 WO | 8/2002 |

OTHER PUBLICATIONS

Nargessi, R. D., "Isolation and Purification of Nucleic Acids", Pending U.S. Appl. No. 10/244,144, filed Sep. 12, 2002.

Taylor, J.I., et al., "Application of Magnetite and SilicaMagnetite Composits to the Isolation of Genomic DNA", J. Chromatography A, 890: 159–166 (2000).

Ahn, S.C., et al.; "Rapid Mini–Scale Plasmid Isolation for DNA Sequencing and Restriction Mapping", BioTechniques, 29:466–468 (2000).

Scott Jr., D.L., et al., "The Use of Biomagnetic Separation to Recover DNA Suitable for PCR From Claviceps Species", Lett. Appl. Microl., 31:95–99 (2000).

Lin, Z., et al., "Protocol for Genomic DNA Preparation From Fresh or Frozen Serum for PCR Amplification", BioTechniques, 29:460–466 (2000).

Mrazek, F. et al., "Processing of mRNA From Human Leukocytes by Biomagnetical Separation: Comparison With Current Methods of RNA Isolation", Acta Univ. Palacki. Olomuc., Fac. Med. 142:23–28 (1999).

Davies, M.J., et al., "Isolation of Plasmid DNA Using Magnetite as a Solid–Phase Adsorbent", Anal. Biochem. 262:92–94 (1998).

(List continued on next page.)

Primary Examiner—Jeffrey Siew
(74) Attorney, Agent, or Firm—Townsend and Townsend and Crew LLP

(57) ABSTRACT

A method for the isolation and purification of nucleic acids such as DNA, RNA, and PNA from various sources using magnetizable cellulose or its derivatives. Adjusting the concentrations of the salt and polyalkylene glycol to the levels that result in binding of nucleic acids to the magnetizable cellulose or its derivatives. Separating the nucleic acids bound to the magnetizable cellulose particles or its derivatives and eluting the nucleic acids from the particles.

31 Claims, 3 Drawing Sheets

Agarose Gel Electrophoresis of DNA isolated from whole blood using MagaCell™ or Qiagen QIAamp DNA Mini Kit, showing high molecular weight DNA isolated by both techniques.

Lane 1: 1 Kb DNA Ladder
Lane 2: Calf thymus DNA Control
Lanes 3, 5, 7, 9, and 11: DNA isolated by MagaCell
Lanes 4, 6, 8, 10, and 12: DNA isolated by QIAamp

OTHER PUBLICATIONS

Levison, P.R., et al., Recent Developments of Magnetic Beads for Use in Nucleic Acid Purification, J. Chromatography A, 816:107–111 (1998).

Rudi, K., et al., "Rapid, Universal Method to Isolate PCR-Ready DNA Using Magnetic Beads", BioTechniques, 22:506–511 (1997).

Kotsopoulos, S.K., et al., "Isolation of 3.5-KB Fragments on Magnetic Solid Supports", BioTechniques, 20:198–200 (1996).

Sambrook, J., et al., "Extraction and Purification of Plasmid DNA", Molecular Cloning, A Laboratory Manual, Second Edition, 1.21–1.45 (1998), Cold Harbor Laboratory Press.

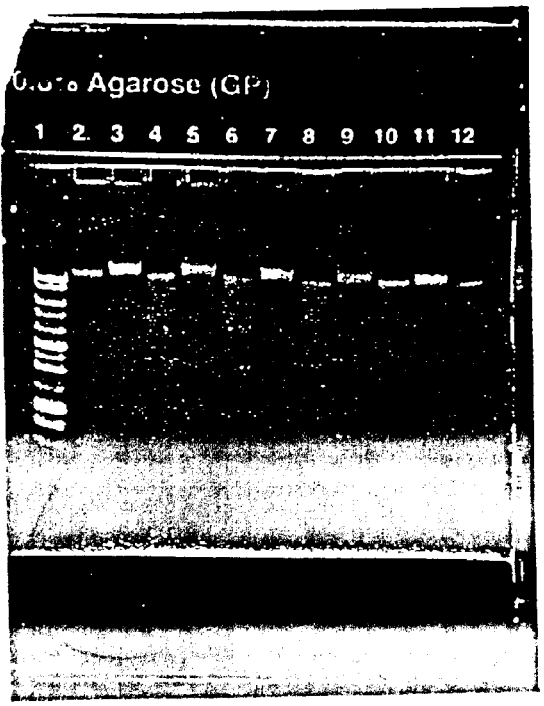
Figure 1. Agarose Gel Electrophoresis of DNA isolated from whole blood using MagaCell™ or Qiagen QIAamp DNA Mini Kit, showing high molecular weight DNA isolated by both techniques.
    Lane 1: 1 Kb DNA Ladder
    Lane 2: Calf thymus DNA Control
    Lanes 3, 5, 7, 9, and 11: DNA isolated by MagaCell
    Lanes 4, 6, 8, 10, and 12: DNA isolated by QIAamp

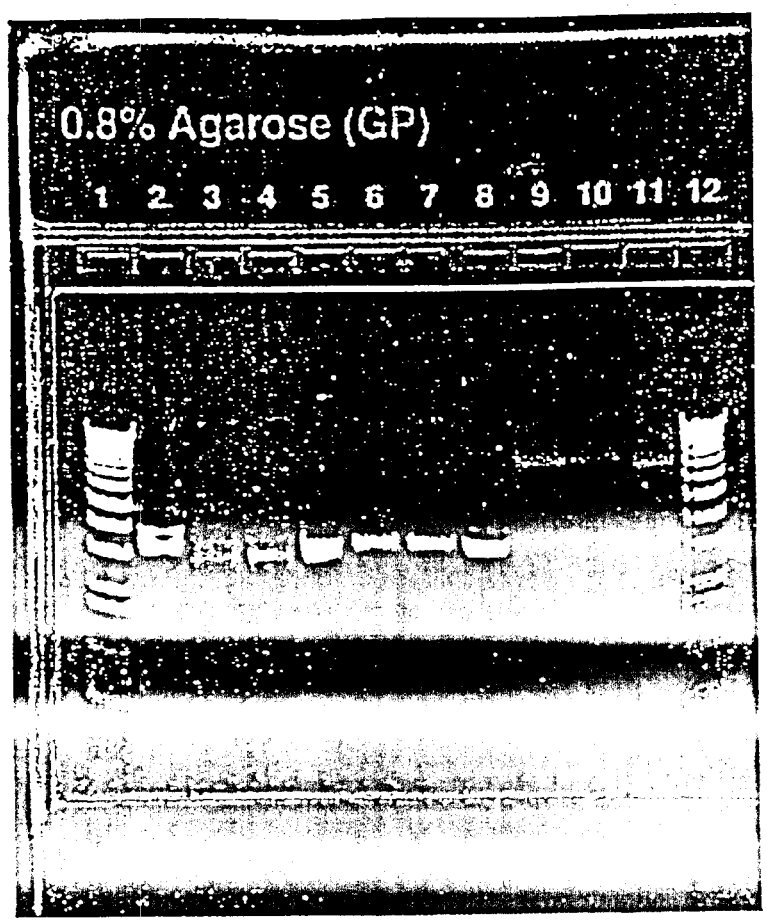

Figure 2. Agarose Gel Electrophoresis of Plasmid DNA Isolated from bacterial cell lysates, using MaCell™ or Qiagen QIAprep Miniprep Kit. Two different sizes of high quality plasmid DNA were isolated by both methods.

Lanes 1 and 12: 1 Kb DNA Ladder
    Lane 2: Plasmid DNA PBA117 Control
    Lanes 3, 4, 6, and 7: Plasmid DNA PBA117 isolated by MagaCell
    Lanes 5 and 8: Plasmid DNA PBA117 isolated by QIAprep Miniprep
    Lanes 9 and 10: Plasmid DNA PBA8 isolated by MagaCell
    Lane 11: Plasmid DNA PBA8 isolated by QIAprep Miniprep

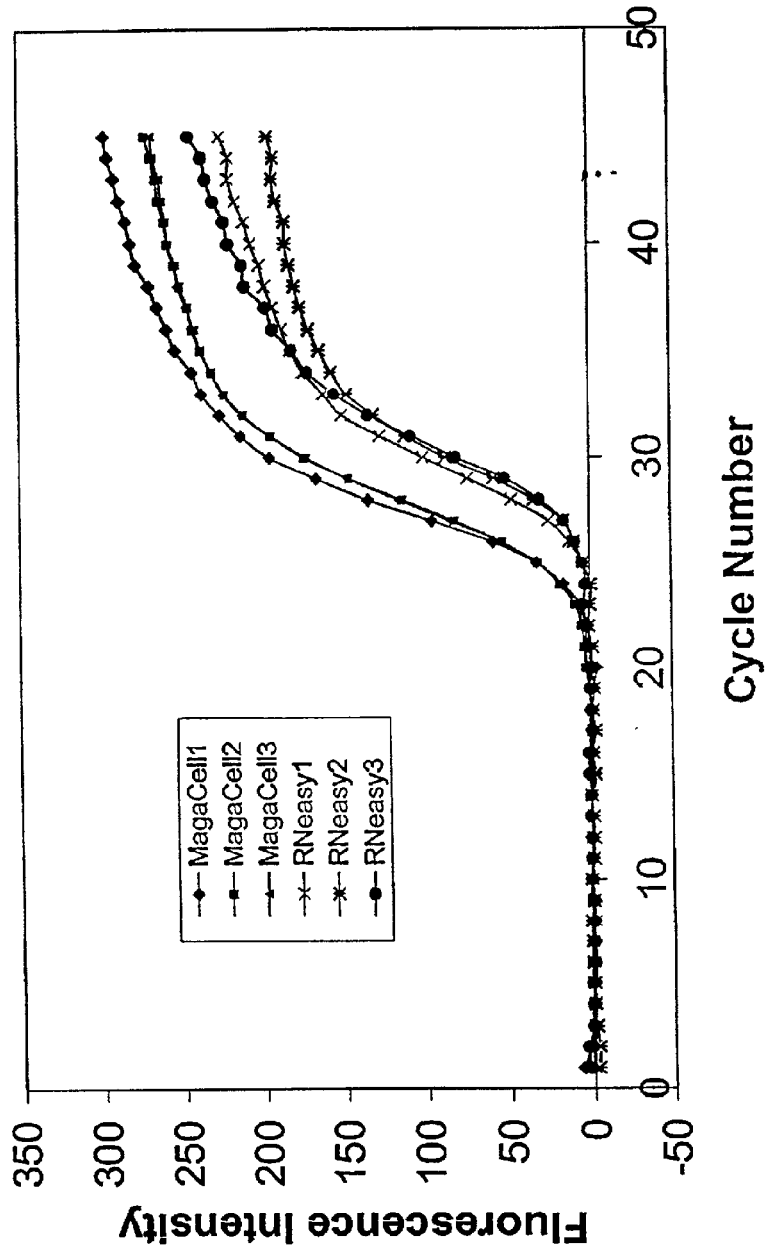

MAGNETIC ISOLATION AND PURIFICATION OF NUCLEIC ACIDS

CROSS-REFERENCES TO RELATED APPLICATIONS

This application claims the benefit of U.S. Ser. No. 60/269,729, filed Feb. 16, 2001, the disclosure of which is incorporated herein by reference.

STATEMENT AS TO RIGHTS TO INVENTIONS MADE UNDER FEDERALLY SPONSORED RESEARCH AND DEVELOPMENT

Not applicable

BACKGROUND OF THE INVENTION

Isolation and purification of high quality nucleic acids are critical steps in molecular biology procedures. A number of methods have been reported for the isolation of single and double stranded DNA from biological fluids such as human blood, serum, cultured cells, as well as plants, animal and human tissues, and other specimens. Many different procedures have been described. See, for example, Taylor, J. I., et al., *J. Chromatograpy A,* 890:159–166 (2000); Ahn, S. C., et al., *BioTechniques,* 29:466–468 (2000); Scott Jr, D. L. et al., *Lett. Appl Microl.,* 31:95–99 (2000); Lin, Z, and Floros, J., *BioTechniques,* 29:460–466 (2000); Smith, C. E. and York, C. K., U.S. Pat. No. 6,027,945 (2000); Mrazek, F. and Petrek, M., *Acta Univ. Palacki. Olomuc., Fac. Med.* 142:23–28 (1999); Hawkins, T., U.S. Pat. No. 5,898,071 (1999); Hawkins, T., U.S. Pat. No. 5,705,628 (1998); Davies, M. J., et al., *Anal. Biochem.* 262:92–94 (1998); Levison, P. R., et al., *J. Chromatography A,* 816:107–111 (1998); Rudi, K., et al., *BioTechniques,* 22:506511 (1997); Kotsopoulos, S. K., and Shuber, A. P., *BioTechniques,* 20:198–200 (1996); Boom, W. R., et al., U.S. Pat. No. 5,234,809 (1993); Reeve, M. A., WO 91/12079 (1991); Sambrook, J., et al., in: MOLECULAR CLONING, A LABORATORY MANUAL, $2^{ND}$ EDITION, 1.21–1.45 (1989), Cold Spring Harbor Laboratory Press. Most of these procedures are time consuming, tedious, and costly. In addition a number of these procedures involve the use of hazardous organic solvents.

SUMMARY OF THE INVENTION

The method described in the present invention, employs particles having magnetic or paramagnetic properties that are encapsulated in a polymer such as cellulose (magnetizable cellulose) or cellulose derivatives. Surprisingly, in the presence of certain chemicals and salts, formulated as a binding buffer, these particles can adsorb nucleic acids.

The nucleic acids bound to the particles are then washed, with a wash buffer, to remove any unwanted materials, and the bound nucleic acid is then eluted from the particles by adding an elution buffer or deionized water.

The magnetizable cellulose and magnetizable cellulose derivatives are supplied by CORTEX BIOCHEM INC., San Leandro, Calif., under the trade name of MagaCell™. They can also be produced using the procedure described by Pourfarzaneh et al, *Methods Biochem. Anal.* 28:267–295 (1982).

The binding buffer will generally contain high salt and polyalkylene glycol concentrations. The concentrations of the resulting combination are adjusted to concentrations suitable for binding of nucleic acids to the magnetizable cellulose or magnetizable cellulose derivatives. The described binding buffer with slight modifications can also be used as the wash buffer.

The present invention also relates to a method of isolating nucleic acids such as DNA, RNA and PNA, from various sources including biological fluids, tissues, cells, and bacteria cell lysates containing plasmids, etc. The method comprises binding of nucleic acids, in presence of a binding buffer, to magnetizable cellulose or its derivatives, washing the resulting bound nucleic acids with a wash buffer, and eluting the nucleic acids with an elution buffer or water.

The methods described herein are also useful for the isolation of both double stranded (ds) or single stranded (ss) polynucleotides (e.g., DNA, RNA, PNA) of virtually any size and from a wide variety of sources.

Still further, the present invention provides a kit comprising magnetizable cellulose or its derivatives and a binding buffer that contains a suitable salt and polyalkylene glycol at concentrations suitable for binding nucleic acids onto magnetizable cellulose or its derivatives. In some embodiments, the kit will also contain a suitable wash buffer, elution buffer, and reagents for lysing cells, tissues or materials from other sources to release the nucleic acids.

BRIEF DESCRIPTION OF THE DRAWINGS

FIG. 1 is an Agarose gel electrophoresis showing DNA isolated from whole blood using MagaCell™ or Qiagen QIAamp DNA Mini Kit, and shows the high molecular weight non-degraded DNA isolated by both techniques. Lane 1 is a 1 Kb DNA ladder, Lane 2 is calf thymus DNA control; Lanes 3, 5, 7, 9, and 11 are DNA isolated by the present method; and Lanes 4, 6, 8, 10 and 12 are DNA isolated by QIAamp.

FIG. 2 is an Agarose gel electrophoresis of plasmid DNA isolated from bacterial cell lysates, using MagaCell™ or Qiagen QIAprep Miniprep Kit, and shows that two different sizes of high quality plasmid DNA were isolated by both techniques. Lanes 1 and 12 are 1 Kb DNA ladders; Lane 2 is plasmid DNA PBA 117 control; Lanes 3, 4, 6, and 7 are plasmid DNA PBA 117 isolated by MagaCell™; Lanes 5 and 8 are plasmid DNA PBA 117 isolated by QIAprep Miniprep; Lanes 9 and 10 are plasmid DNA PBA8 isolated by MagaCell™; and Lane 11 is plasmid DNA PBA8 isolated by QIAprep Miniprep.

FIG. 3 is a graph illustrating the real time RT-PCR quantitation of MS2 Viral RNA isolated by MagaCell™ or RNeasy Kit.

DETAILED DESCRIPTION OF THE INVENTION

General

The present method simplifies the isolation of nucleic acids from various sources by eliminating the need for centrifugation or organic solvents including alcohol extraction or washes, and produces nucleic acids ready for further characterization and downstream processing such as PCR, sequencing or blotting procedures. Because of the unique features described herein, the present method is readily adaptable to automation including high throughput screening systems.

Additionally, the iron oxide, cellulose and cellulose derivatives used for the production of magnetizable cellulose in the present invention are commercially available and inexpensive. The method described herein also avoids the lengthy procedure and use of hazardous chemicals involved in the preparation and modification of the magnetic particles described in Hawkins, U.S. Pat. No. 5,898,071. Still further, the present methods eliminate the need for chemical synthesis of various functional groups, a requirement for particles described in Hawkins, U.S. Pat. No. 5,898,071 to bind DNA. Hawkins, ibid. notes that microparticles with a cellulose/iron oxide core did not bind DNA in their methods. Quite surprisingly, the magnetizable cellulose and methods described herein were both efficient in isolating DNA and were inexpensive, providing a significant improvement in DNA isolation and purification over the methods of Hawkins.

Description of the Embodiments

In the methods below, magnetizable cellulose or magnetizable cellulose derivatives were found to bind to nucleic acids, in presence of certain concentrations of salt and polyalkylene glycol. Accordingly, the present invention provides in one aspect, a method for simple and rapid isolation of nucleic acids, such as DNA, RNA and PNA, from various sources, including but not limited to body fluids, various solutions, cells, plants, tissues, bacterial cell lysates containing plasmids, etc. Also the invention described is for the isolation of nucleic acids on the basis of size. The following is a description of the present invention with reference to nucleic acids as exemplified by DNA. It is to be understood that the present invention is also useful for separation of RNA and PNA in a similar manner. Because small nucleic acids require higher salt concentrations for strong binding to the magnetizable cellulose particles, salt concentration can be selectively manipulated to release nucleic acids bound to magnetizable cellulose on the basis of size. The magnetizable cellulose having DNA bound thereto can, optionally, be washed with a suitable wash buffer before they are contacted with a suitable elution buffer, to elute and separate the DNA from magnetizable cellulose. Separation of magnetizable cellulose from the liquid during all the isolation steps can be simplified by, for example, applying a magnetic field to draw down or draw to the side the magnetizable cellulose particles.

In view of the above, the present invention provides in one aspect, a method to bind nucleic acids to magnetizable cellulose comprising:

a) combining magnetizable cellulose with a solution containing nucleic acids, thereby producing a combination, and b) adjusting the salt and polyalkylene glycol concentrations of the combination to concentrations suitable for binding the nucleic acids onto the magnetizable cellulose, whereby all or a portion of the nucleic acids in the solution bind to the magnetizable cellulose.

The amount of nucleic acids that are bound to the magnetizable cellulose will typically depend on the amount of magnetizable cellulose. Preferably, the amount of magnetizable cellulose is sufficient to avoid saturation of the cellulose particle surface and at least 60%, more preferably 80% and still more preferably 90% or more of the nucleic acids in a solution are bound to the magnetizable cellulose. In many instances, the portion of nucleic acids bound will be 100%. In some embodiments, however, selective binding of nucleic acids of a particular size can be achieved by manipulation of the salt and polyalkylene glycol concentrations such that only about 5% to about 30% of the total nucleic acid content in a sample is bound to the magnetizable cellulose.

In the methods of the present invention, the magnetizable cellulose can be purchased from Cortex Biochem Inc., San Leandro, Calif. Alternatively, the particles can be produced using the procedure described by Pourfarzaneh et al, *Methods Biochem. Anal.* 28, 267–295 (1982). The iron oxide, cellulose and cellulose derivatives used for the production of magnetizable cellulose or magnetizable cellulose derivatives are also commercially available and are inexpensive.

As described in the present invention, the binding of nucleic acids to the magnetizable cellulose or its derivatives and removal of the non-specifically adsorbed proteins or other substances can be achieved using a solution of salt and polyalkylene glycol at certain concentrations. Useful salts in the present invention are selected from LiCl, $BaCl_2$, $MgCl_2$, $CsCl_2$, $CaCl_2$, NaCl, KCl and KI. Preferably the salt is NaCl. Similarly, a variety of polyalkylene glycols are useful in the present invention including, for example, polyethylene glycol and polypropylene glycol. Preferably, the polyalkylene glycol is polyethylene glycol. The salt and polyalkylene reagents are used in concentrations that facilitate binding of nucleic acids to the cellulose coated magnetizable particles and its derivatives. Salt concentrations in the binding and wash buffers will depend on the salt being used and milieu from which the nucleic acids are to be isolated and purified. Generally, the salt concentrations will be about 0.25 M to about 5.0 M. More preferably, the salt concentration in the binding and wash buffers is about 0.5 M to about 2.5 M. Still more preferably, salt concentration is about 0.5 M to about 1.5 M. Most preferably, the salt concentration of the binding buffer is about 1.25 M and the salt concentration of the wash buffer is about 0.5 M. Similarly, the polyalkylene concentration will depend on the polyalkylene used. Polyethylene glycol is commercially available from suppliers such as Sigma Chemical Company (St. Louis, Mo., USA) and is useful in molecular weights of about 1,000 to about 10,000, preferably about 6,000 to about 8,000. Depending on the weight range of polyethylene glycol used, the concentration can be adjusted. Generally, for methods in which polyethylene glycol having an average molecular weight of 8,000 is used, the concentration in the binding and wash buffers will be adjusted to about 5% to about 15%, preferably about 10%.

The use of the binding and wash buffers described above, and in the examples below, avoids the use of organic solvents, including ethyl alcohol, commonly used with other DNA isolation procedures.

In the present invention, the magnetizable cellulose is in the form of particles and preferably has an iron oxide content of up to about 90% by weight of the total mass of the magnetizable cellulose. The magnetic component of the magnetizable cellulose can be replaced by other magnetic compounds such as ferrous oxide or nickel oxide, etc.

In a related aspect, the present invention provides a method of separating nucleic acids from non-nucleic acid materials by binding nucleic acids in a nucleic acid solution to magnetizable cellulose, comprising:

a) combining magnetizable cellulose with a solution containing nucleic acids and non-nucleic acid materials to produce a first combination;

b) adjusting the salt and polyethylene glycol concentrations of the first combination to concentrations suitable for binding nucleic acids in the solution to the magnetizable cellulose, producing a second combination comprising magnetizable cellulose-bound nucleic acids;

c) separating the magnetizable cellulose-bound nucleic acids from the second combination;

d) contacting the magentizable cellulose-bound nucleic acids separated in c) with an elution buffer to release the bound nucleic acids from the magnetizable cellulose and into the elution buffer; and e) separating the magnetizable cellulose from the elution buffer to provide nucleic acids that are substantially free of the non-nucleic acid materials.

In general, the components used in this aspect of the invention are the same as have been described above, and the preferred ranges for salts and polyethylene glycol concentrations are the same as provided above. The elution buffer is preferably a Tris buffer with EDTA. More preferably the elution buffer is about 10 mM Tris, pH 8.0 with about 1 mM EDTA. Also, as noted above, this aspect of the invention can be used with a variety of nucleic acids including, for example, DNA, RNA, PNA or mixtures thereof.

In a particularly preferred embodiment of this aspect of the invention, the nucleic acids bound to magnetizable cellulose particles are DNA and are washed with a wash buffer, wherein the wash buffer removes impurities bound to the magnetizable cellulose particles while leaving the DNA bound to the magnetizable cellulose particles. More preferably, the DNA bound to the magnetizable cellulose particles is eluted with an elution buffer that releases the DNA bound to the magnetizable particles, and the DNA is isolated.

In other preferred embodiments, the nucleic acids in solution are a lysate, preferably prepared from cells of human, plant, animal, viral or bacterial origin. Thus, in one application, the cells are from animals, more preferably humans. In another application, the cells are from plants. In another application, the cells are of bacterial origin. In still another application, the cells are of viral origin.

The nucleic acids that are separated from non-nucleic acid materials (e.g., peptides, proteins, oligosaccharides, lignans, small molecule natural products and other materials typically of natural origin) are generally obtained in a purity of at least 80%, more preferably at least 90%, still more preferably at least 95%, and most preferably at least 99% or more. Accordingly, the present methods are suitable to remove at least 80%, more preferably at least 90%, still more preferably at least 95%, and most preferably at least 99% or more of the non-nucleic acid materials in a particular sample (e.g., a cell lysate).

In yet another aspect of the invention, magnetizable cellulose derivatives are used. Accordingly, the invention provides a method to bind nucleic acids to magnetizable cellulose derivatives comprising:

a) combining magnetizable cellulose derivatives with a solution containing nucleic acids, thereby producing a combination; and b) adjusting the salt and polyalkylene glycol concentrations of the combination to concentrations suitable for binding the nucleic acids onto the magnetizable cellulose derivatives, whereby all or a portion of the nucleic acids in the solution bind to the magnetizable cellulose derivatives.

Again, the preferred components and amounts are essentially as provided above. The magnetizable cellulose derivatives are, in one group of embodiments, selected from cellulose-CM, cellulose-DEAE and mixtures thereof. Additionally, this method as well as the other methods of the present invention find wide application in the purification of, for example, DNA, RNA, PNA or derivatives thereof In related methods, the present invention provides a method of separating nucleic acids from non-nucleic acid materials, comprising:

a) combining magnetizable cellulose derivatives with a solution containing nucleic acids and non-nucleic acid materials to provide a first combination;

b) adjusting the salt and polyethylene glycol concentrations of the first combination to concentrations suitable for binding nucleic acids to the magnetizable cellulose derivatives, producing a second combination comprising magnetizable cellulose derivative-bound nucleic acids;

c) separating the magnetizable cellulose derivative-bound nucleic acids from the second combination;

d) contacting the magnetizable cellulose derivative-bound nucleic acids separated in c) with an elution buffer to release the bound nucleic acids from the magnetizable cellulose derivatives and into the elution buffer; and e) separating the magnetizable cellulose derivatives from the elution buffer to provide nucleic acids that are substantially free of the non-nucleic acid materials.

Preferred embodiments for this aspect of the invention are those that have been described above for the use of magnetizable cellulose. Also, as above, the magnetizable cellulose derivatives are, in one group of embodiments, selected from cellulose-CM, cellulose-DEAF and mixtures thereof.

The present invention will now be illustrated by the following examples, which are not limiting in any way.

General Methodology

The magnetizable particles used in the following examples were the MagaCell Particles or its derivatives from Cortex Biochem Inc., San Leandro, Calif., or were made by the procedure described by Pourfarzaneh et al, *Methods Biochem. Anal.* 28:267–295 (1982). The particles were stored in deionized water, containing 0.02% sodium azide, at a concentration of 50 mg/mL. All agarose gel electrophoresis were run using E-Gel System (0.8% agarose gels) from Invitrogen, Carlsbad, Calif.

EXAMPLE 1

DNA Isolation Using Magnetizable Cellulose

A calf thymus DNA preparation (Sigma, St. Louis, Mo., Catalog Number:

D1501), used as a control, was reversibly bound to MagaCell™ (magnetizable cellulose) Particles in the presence of the binding buffer. The DNA bound to magnetizable cellulose particles was separated and washed from unwanted materials. DNA was then eluted from the particles. The following procedure was used:

1. In a 2 ml microcentrifuge tube containing 50 μg (50 μl of a 1 mg/ml DNA solution in TE buffer (10 mM Tris-HCl, pH 8.0, 1 mM EDTA) add 430 μl of the Binding Buffer (10% PEG 8000 MW, 1.25 M NaCl) and 1 mg (20 μl of a 50 mg/ml suspension) of the MagaCell Particles (Cortex Biochem, Calif.).

2. Mix the tube content at room temperature for 10 minutes, using an end-over-end rotator.

3. Sediment the DNA bound to MagaCell Particles using a magnetic rack.

4. Wash particles with the Wash Buffer (10% PEG 8000 MW, 2.5 M NaCl). Repeat the wash step once more.

5. Elute the DNA from MagaCell Particles using the Elution Buffer (deionized water or TE Buffer [10 mM Tris-HCl, pH 8.0, 1 mM EDTA]).

Agarose gel electrophoresis of the eluted DNA showed a single non-degraded high molecular weight DNA band (FIG. 1).

EXAMPLE 2

DNA Isolation Using Magnetizable Cellulose Derivatives

Example 1, described above was repeated using magnetizable cellulose derivatives. These included: MagaCell™-CM and MagaCell™-DEAE (both obtained from Cortex Biochem, San Leandro, Calif.).

Results obtained with the MagaCell™ derivatives were comparable to those obtained by MagaCell™.

EXAMPLE 3

DNA Isolation from Whole Blood Using Magnetizable Cellulose

DNA from human whole blood samples was released using proteinase K and a specially formulated lysis buffer. The DNA was then bound to MagaCell Particles in presence of the Binding Buffer. The DNA bound to MagaCell Particles was then separated and washed from other contaminants. The DNA was eluted from the particles. The following procedure was used:

1. Into a 2 ml microcentrifuge tube, pipet 20 $\mu$l (400 $\mu$g) of proteinase K solution in 10 mM Tris-HCl, 1 mM Calcium Chloride, 50% glycerol, pH 7.5.
2. Add 200 $\mu$l of whole blood (heparin-, citrate- or EDTA-treated).
3. Add 200 $\mu$l of the Lysis Buffer (50 mM Tris-HCl, 50 mM EDTA, 6 M Guanidine-HCl, 6 M Urea, 10 mM Calcium Chloride, 10% Tween-20, pH 6.3).
4. Mix the tube content by pulse-vortexing for 15 sec.
5. Incubate the tube content at 56° C. for 10 minutes.
6. Remove the tube from 56° C., and add 560 $\mu$l of the Binding Buffer (10% PEG 8000 MW, 1.25 M NaCl), followed by 20 $\mu$l (1 mg) of the well-mixed MagaCell suspension (50 mg/ml in deionized water, containing 0.02% Sodium Azide).
7. Incubate the tube content for 10 min at room temperature, while mixing on an end-over-end rotator.
8. Sediment the MagaCell bound DNA particles using a magnetic rack.
9. Aspirate the supernate and wash the particles by adding 1 ml of the Wash Buffer (10% PEG 8000 MW, 2.5 M NaCl), mixing well and aspirating the supernate. Repeat the wash step once.
10. Add 500 $\mu$l of the Elution Buffer (10 mM Tris-HCl, pH 8.0, 1 mM EDTA) or deionized water, and mix for 10 min as in Step 7.
11. Sediment the particles and carefully collect the supernate containing the purified DNA.
12. The purified DNA is then ready for further analysis.

Agarose gel electorphoresis of the DNA isolated from whole blood samples by the method of present invention showed a single non-degraded high molecular weight DNA band (FIG. 1).

Downstream processing of the DNA isolated from whole blood samples by the method of present invention indicated suitability of the isolated DNA for PCR application (Tables 1 and 2).

TABLE 1

DNA Yield From Whole Blood Using MagaCell ™ Or QIAGEN QIAamp DNA Mini Kit

| Sample ID | PCR Quantitation ($\mu$g) | | $A_{260}$ Quantitation ($\mu$g) | |
|---|---|---|---|---|
| | MagaCell ™ | QIAamp | MegaCell ™ | QIAamp |
| A | 12.13 | 12.61 | 10.57 | 6.01 |
| B | 6.13 | 5.91 | 8.75 | 4.89 |
| C | 4.84 | 7.11 | 8.23 | 5.24 |
| D | 6.11 | 5.97 | 8.28 | 4.14 |
| E | 3.84* | 9.58 | 7.10* | 6.95 |

*Eluted only once.

TABLE 2

DNA Yield From Whole Blood Using MagaCell ™ Or QIAGEN QIAamp DNA Mini Kit

| Sample ID | MegaCell ™ DNA Copies (Total) | QIAamp DNA Copies (Total) |
|---|---|---|
| A | $1.17 \times 10^{6*}$ | $2.91 \times 10^6$ |
| B | $3.69 \times 10^6$ | $3.84 \times 10^6$ |
| C | $3.71 \times 10^6$ | $1.80 \times 10^6$ |
| D | $4.64 \times 10^6$ | $2.16 \times 10^6$ |
| E | $6.14 \times 10^6$ | $1.82 \times 10^6$ |

*Eluted only once.

The method described herein is simple, fast, economical, and produces high-yield purified DNA, comparable to or better than those produced by using a leading supplier of the DNA isolation product (Qiagen, Valencia, Calif.).

EXAMPLE 4

DNA Isolation Using Magnetizable Cellulose and a Modified Wash Buffer

Calf thymus DNA (Sigma, St. Louis, Mo., Catalog Number: D1501) was processed and analyzed as in Example 1, except that for washing of the MagaCell bound DNA particles (Step 4) the Wash Buffer was modified to contain 10% PEG 8000 MW and 0.25 M NaCl.

EXAMPLE 5

DNA Isolation from Whole Blood Using Magnetizable Cellulose and a Modified Wash Buffer DNA from whole blood samples was isolated and analyzed as in Example 3, except that for washing of the MagaCell bound DNA particles (Step 9) the Wash Buffer was modified to contain 10% PEG 8000 MW and 0.25 M NaCl.

EXAMPLE 6

DNA Isolation from Buffy Coat Using Magnetizable Cellulose

DNA from 200 $\mu$l buffy coat samples (a leukocyte-enriched fraction of whole blood, obtained from Fred Hutchinson Cancer Research Center, Seattle, Wash.) was isolated and analyzed as in Example 3.

EXAMPLE 7

DNA Isolation from Buffy Coat Using Magentizable Cellulose and a Modified Wash Buffer DNA from 200 $\mu$l buffs coat samples (a leukocyte-enriched fraction of whole blood, obtained from Fred Hutchinson Cancer Research Center, Seattle, Wash.) was isolated and analyzed as in Example 5.

EXAMPLE 8

DNA Isolation from Cultured Cells Using Magnetizable Cellulose

DNA from cultured cells (maximum $2.5 \times 10^7$ cells) suspended in 200 µl PBS (Phosphate Buffered Saline) was isolated and analyzed as in Example 3.

EXAMPLE 9

DNA Isolation from Cultured Cells Using Magnetizable Cellulose and a Modified Wash Buffer DNA from cultured cells (maximum $2.5 \times 10^7$ cells) suspended in 200 µl PBS (Phosphate Buffered Saline) was isolated and analyzed as in Example 5.

EXAMPLE 10

DNA Isolation from Plant Tissue Using Magnetizable Cellulose

DNA from Arabidopsis plant leaves (obtained from Department of Plant Biology, University of Davis, Davis, Calif.) was released using Proteinase K (PK) and a Lysis Buffer. The DNA was then bound to MagaCell Particles in presence of the Binding Buffer. The DNA bound to MagaCell Particles was then separated and washed from other contaminants. The DNA was eluted from the particles. The following procedure was used:

1. Place 25–100 mg of a well-ground plant tissue at the bottom of a 2 ml microcentrifuge tube.
2. Add 200 µl of the Lysis Buffer A (Buffer ATL, Qiagen, Valencia, Calif., Catalog Number: 19076), followed by 20 µl of the PK Solution. Mix gently by pulse vortexing. Note: If RNA-free DNA preparation is required, add 10 µl of a 40 mg/ml RNase A stock solution before addition of the Plant Lysis Buffer.
3. Incubate at 65° C. for 15 minutes.
4. Remove the tube from 65° C.
5. Centrifuge at maximum speed in a microcentrifuge for 5 min.
6. Gently transfer the supernate into a clean 2 ml microcentrifuge tube.
7. Add 500 µl of the Binding Buffer (10% PEG 8000 MW, 1.25 M NaCl), followed by 20 µl of the well-mixed (particles are uniformly suspended) MagaCell Particles.
8. Mix the tube gently and incubate for 10 min at room temperature, while mixing (using an end-over-end rotator or manual mixing).
9. Sediment the MagaCell bound DNA particles using a magnetic rack. Aspirate the supernate and wash particles as described in Step 10.
10. Add 1 ml Wash Buffer (10% PEG 8000 MW, 1M NaCl) to the tube from Step 9. Mix well, sediment the particles on the magnetic rack and aspirate the supernate.
11. Repeat the wash once more by following Step 10.
12. Add 200 µl of the Elution Buffer (10 mM Tris, pH 8.0, 1 mM EDTA) or deionized water and mix for 10 min as in Step 8.
13. Sediment the particles and carefully transfer the supernate containing the isolated DNA into a clean tube. The material is ready for further analysis. If the sample is not going to be tested on the same day, freeze at −20° C. until the time of analysis.

EXAMPLE 11

DNA Isolation from Plant Tissue Using Magnetizable Cellulose and a Modified Wash Buffer DNA from Arabidopsis plant leaves (obtained from Department of Plant Biology, University of Davis, Davis, Calif.) was released and analyzed as in Example 10, except that for washing of the MagaCell bound DNA particles (Step 10) the Wash Buffer was modified to contain 10% PEG 8000 MW and 0.25 M NaCl.

EXAMPLE 12

DNA Isolation form Fish Fin Tissue Using Magnetizable Cellulose

DNA from Fish fin tissue (obtained from Bodega Marine Lab, University of Davis, Davis, Calif.) was released using Proteinase K (PK) and two different Lysis Buffers. The DNA was then bound to MagaCell Particles in presence of the Binding Buffer. The DNA bound to MagaCell Particles was then separated and washed from other contaminants. The DNA was eluted from the particles. The following procedure was used:

1. Place ~5 mg of a fish fin tissue at the bottom of a 2 ml microcentrifuge tube.
2. Add 200 µl of the Lysis Buffer A (Buffer ATL, Qiagen, Valencia, Calif., Catalog Number: 19076), followed by 20 µl of the PK Solution. Mix gently by pulse vortexing. Note: If RNA-free DNA preparation is required, add 10 µl of a 40 mg/ml RNase A stock solution before addition of Lysis Buffer A.
3. Incubate at 56° C. with occasional mixing for 1 hour.
4. Remove the tube from 56° C.
5. Add 200 µl of the Lysis Buffer B (50 mM Tris-HCl, 50 mM EDTA, 6 M Guanidine-HCl, 6 M Urea, 1 0 mM Calcium Chloride, 10% Tween-20, pH 6.3).
6. Incubate at 70° C. for 10 minutes, then remove the tube from 70° C.
7. Add 500 µl of the Binding Buffer (10% PEG 8000 MW, 1.25 M NaCl) followed by 20 µl of the well-mixed (particles are uniformly suspended) MagaCell Particles.
8. Mix the tube gently and incubate for 10 min at room temperature, while mixing (using an end-over-end rotator or manual mixing).
9. Sediment the MagaCell bound DNA particles using a magnetic rack. Aspirate the supernate and wash particles as described in Step 10.
10. Add 1 ml Wash Buffer (10% PEG 8000 MW, 0.5 M NaCl) to the tube from Step 9. Mix well, sediment the particles on the magnetic rack and aspirate the supernate.
11. Repeat the wash once more by following Step 10.
12. Add 200 µl of the Elution Buffer (10 mM Tris, pH 8.0, 1 mM EDTA) or deionized water and mix for 10 min as in Step 8.
13. Sediment the particles and carefully transfer the supernate containing the isolated DNA into a clean tube. The material is ready for further analysis. If the sample is not going to be tested on the same day, freeze at −20° C. until the time of analysis.

EXAMPLE 13

DNA Isolation form Fish Fin Tissue Using Magnetizable Cellulose and a Modified Wash Buffer

DNA from Fish fin tissue (obtained from Bodega Marine Lab, University of Davis, Davis, Calif.) was isolated and analyzed as in Example 12, except that for washing of the MagaCell bound DNA particles (Step 10), the Wash Buffer was modified to contain 10% PEG 8000 MW and 0.25 M NaCl.

EXAMPLE 14

Plasmid DNA Isolation from Bacterial Cells Using Magnetizable Cellulose

Plasmid DNA (PBAS and PBA 117, obtained from Prozyme, San Leandro, Calif.) was released from bacterial cell culture (*E.coli*; XL1-Blue) using a modified alkaline lysis procedure. Briefly, the bacterial cells were pelleted by centrifugation in a microcentrifuge tube. The pellet was resuspended in a Resuspension Buffer. The cells were then lysed by Sodium Hydroxide containing SDS, followed by neutralization with Potassium Acetate. The cell lysate was then cleared by centrifugation and the supernate was used for plasmid DNA isolation by the present invention. Thus the plasmid DNA in the supernate was bound to MagaCell Particles in presence of a specially formulated Binding buffer. The DNA bound to MagaCell Particles was then separated and washed from other contaminants. The DNA was eluted from the particles. The following procedure was used:

1. Resuspend the bacterial pelleted cells in 150 μl of the Resuspension Buffer (50 mM Tris, 10 mM EDTA, pH 8.0 containing 100 μg/ml RNase A, Sigma, St. Louis, Mo., Catalog Number: R4642) and transfer to a clean 2 ml microcentrifuge tube.
2. Add 150 μl of Solution A (0.2 M Sodium Hydroxide, 1% SDS). Gently invert the tube for 4–6 times to mix until the solution becomes viscous and slightly clear.
3. Add 150 μl of Solution B (3 M Potassium Acetate, pH 5.5) and invert the tube immediately but gently 4–6 times until the solution becomes cloudy.
4. Centrifuge at high speed for 10 min.
5. Carefully remove the superanate and transfer into a clean 2 ml microcentrifuge tube.
6. Add 500 μl of the Binding Buffer (10% PEG 8000 MW, 1.25 M NaCl) followed by 20 μl of the well-mixed particles are uniformly suspended) MagaCell Particles.
7. Mix the tube gently and incubate for 10 min at room temperature, while mixing (using an end-over-end rotator or manual mixing).
8. Sediment the MagaCell bound DNA particles using a magnetic rack. Aspirate the supernate and wash particles as described in Step 9.
9. Add 1 ml Wash Buffer (10% PEG 8000 MW, 1 M NaCl) to the tube from Step 8. Mix well, sediment the particles on the magnetic rack and aspirate the supernate.
10. Repeat the wash once more by following Step 9.
11. Add 200 μl of the Elution Buffer (10 mM Tris, pH 8.0, 1 mM EDTA) or deionized water and mix for 10 min as in Step 7.
12. Sediment the particles and carefully transfer the supernate containing the isolated DNA into a clean tube. The material is ready for further analysis. If the sample is not going to be tested on the same day, freeze at −20° C. until the time of analysis.

Agarose gel electrophoresis of two different plasmid DNA samples isolated from bacterial cell lysates, using the present method of invention, showed results comparable to those obtained by QIAprep Miniprep (Qiagen, Valencia, Calif.), the leading supplier of plasmid DNA isolation kits (FIG. 2).

EXAMPLE 15

Plasmid DNA Isolation from Bacterial Cells Using Magnetizable Cellulose and a Modified Wash Buffer

Plasmid DNA (PBA8 and PBA117, obtained from Prozyme, San Leandro, Calif.) was released from bacterial cell culture (*E.coli*; XL1-Blue), isolated to high purity, and analyzed as in Example 14, except that for washing of the MagaCell bound DNA particles (Step 9) the Wash Buffer was modified to contain 10% PEG 8000 MW and 0.25 M NaCl.

EXAMPLE 16

Isolation of RNA from Serum Using Magnetizable Cellulose

MS2 viral RNA ($1\times10^7$–$1\times10^8$ copies) was spiked into three different serum samples. The RNA in each sample was then isolated as in Example 3. The purified RNA was then quantitated by MS2 RT-PCR assay using the following template:

| Reagent | 25 μl Reaction | Notes |
|---|---|---|
| DEPC-treated water* | 10.125 μl | |
| 5 × EZ Buffer | 5.0 μl | |
| MS2 Primer 1029F (10 μM) | 0.75 μl | 5'GGAGAGACAGGGCACTGCTA3' |
| MS2 Primer 1096R (10 μM) | 0.75 μl | 5'TTGGCCATACGGATTGTACC3' |
| MS2 Probe 1052T (10 μM) | 0.375 μl | 5'CCCAAATCTCAGCCATGCATCGAG3' |
| SUPERase · In (20 U/μl) | 0.5 μl | |
| dNTPs (2.5 mM) | 3.0 μl | |
| rTth DNA Polymerase | 1.0 μl | |
| Mn(OAc)$_2$ (25 mM) | 2.5 μl | |
| MS2 RNA* | 1.0 μl | |

*Any combination of water and MS2 RNA template can be used as long as the total reaction volume equals 25 μl.

The reaction mixtures were cycled in a Smart Cycler (Cepheid, Sunnyvale, Calif.) using the following conditions: 60° C. for 30 minutes followed by 95° C. for 120 seconds and 45 cycles of 95° C. for 15 seconds, 60° C. for 30 seconds with Optics on.

The MS2 viral RNA was from Bochringer Mannheim, Indianapolis, Ind., Catalog Number: 165948 and MS2.

Primers and Probe were from Oswel, Souhhampton, U.K. GenAmp EZ rTth RNA PCR Kit, Part Number: N808-40179 was from Perkin Elmer and SUPERase•In, an RNase inhibitor, was from Ambion, Austin, Tex. The RNeasy Mini Kit (Qiagen, Valencia, Calif.) was used as the reference method.

Real Time RT-PCR quantitation of MS2 viral RNA isolated by the present method of invention is shown in FIG. 3.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method to bind nucleic acids to magnetizable cellulose comprising
    a) combining magnetizable cellulose with a solution containing nucleic acids, thereby producing a combination, and
    b) adjusting the salt and polyalkylene glycol concentrations of the combination to concentrations suitable for binding the nucleic acids to the magnetizable cellulose, whereby all or a portion of the nucleic acids in the solution binds to the magnetizable cellulose.

2. The method of claim 1, wherein the nucleic acids are DNA and the polyalkylene glycol is polyethylene glycol.

3. The method of claim 2, wherein the polyethylene glycol has a molecular weight of 8000, and wherein the salt is sodium chloride.

4. The method of claim 3, wherein the concentration of polyethylene glycol is adjusted to about 10% and wherein the concentration of sodium chloride is adjusted to between 0.25 M and 5.0 M.

5. The method of claim 1, wherein the nucleic acids are RNA and the polyalkylene glycol is polyethylene glycol.

6. The method of claim 1, wherein the magnetizable cellulose is in the form of particles and optionally contains up to 90% by weight magnetic iron oxide.

7. A method of separating nucleic acids front non-nucleic acid materials in a nucleic acid solution, comprising:
    a) combining magnetizable cellulose with a solution containing nucleic acids and non-nucleic acid materials to produce a first combination;
    b) adjusting the salt and polyethylene glycol concentrations of the first combination to concentrations suitable for binding nucleic acids in the solution to the magnetizable cellulose, producing a second combination comprising magnetizable cellulose-bound nucleic acids;
    c) separating the magnetizable cellulose-bound nucleic acids from the second combination;
    d) contacting the magentizable cellulose-bound nucleic acids separated in c) with an elution buffer to release the bound nucleic acids from the magnetizable cellulose and into the elution buffer; and
    e) separating the magnetizable cellulose from the elution buffer to provide nucleic acids that are substantially free of the non-nucleic acid materials.

8. The method of claim 7, wherein the separation of the magnetizable cellulose particles in step c)and e) is carried out magnetically.

9. The method of claim 8, wherein the nucleic acids bound to magnetizable cellulose particles are DNA and are washed with a wash buffer, wherein the wash buffer removes impurities bound to the magnetizable cellulose particles while leaving the DNA bound to the magnetizable cellulose particles.

10. The method of claim 9, wherein the DNA bound to the magnetizable cellulose particles is eluted with an elution buffer that releases the DNA bound to the magnetizable particles.

11. The method of claim 10, wherein the DNA released by the elution buffer is isolated.

12. The method of claim 7, wherein the polyethylene glycol has a molecular weight of 8000, and wherein the salt is sodium chloride.

13. The method of claim 12, wherein the concentration of polyethylene glycol is about 10%, and concentration of sodium chloride is between 0.25 M to 5.0 M.

14. The method of claim 7, wherein the nucleic acids and non-nucleic acid materials are obtained from a cell lysate.

15. The method of claim 14, wherein the lysate is prepared from cells of human, animal, plant, viral or bacterial origin.

16. A method to bind nucleic acids to magnetizable cellulose derivatives, comprising:
    a) combining magnetizable cellulose derivatives with a solution containing nucleic acids, thereby producing a combination, and
    b) adjusting the salt and polyalkylene glycol concentrations of the combination to concentrations suitable for binding the nucleic acids to the magnetizable cellulose derivatives, whereby all or a portion of the nucleic acids in the solution bind to the magnetizable cellulose derivatives.

17. The method of claim 16, wherein the cellulose derivatives are selected from the group consisting of cellulose-CM, cellulose-DEAE and combinations thereof.

18. The method of claim 16, wherein the nucleic acids are DNA and the polyakylene glycol is polyethylene glycol.

19. The method of claim 16, wherein the nucleic acids are RNA and the polyakylene glycol is polyethylene glycol.

20. The method of claim 18, wherein the polyethylene glycol has an average molecular weight of about 8000, and wherein the salt is sodium chloride.

21. The method of claim 20, wherein the concentration of the polyethylene glycol is adjusted to about 10% and wherein the concentration of sodium chloride is adjusted to between 0.25 M and 5.0 M.

22. The method of claim 16, wherein the magnetizable cellulose derivatives are in the form of particles and optionally comprise magnetic iron oxide in an amount of up to 90% by weight.

23. A method of separating nucleic acids from non-nucleic acid materials, comprising:
    a) combining magnetizable cellulose derivatives with a solution containing nucleic acids and non-nucleic acid materials to provide a first combination;
    b) adjusting the salt and polyethylene glycol concentrations of the first combination to concentrations suitable for binding nucleic acids to the magnetizable cellulose derivatives, producing a second combination comprising magnetizable cellulose derivative-bound nucleic acids;
    c) separating the magnetizable cellulose derivative-bound nucleic acids from the second combination;
    d) contacting the magnetizable cellulose derivative-bound nucleic acids separated in c) with an elution buffer to release the bound nucleic acids from the magnetizable cellulose derivatives and into the elution buffer; and e) separating the magnetizable cellulose derivatives from the elution buffer to provide nucleic acids that are substantially free of the non-nucleic acid materials.

24. The method of claim 23, wherein the separation of the magnetizable cellulose derivatives in step c) and e) is carried out magnetically.

25. The method of claim 23, wherein the nucleic acids bound to magnetizable cellulose derivatives are washed with a wash buffer, wherein the wash buffer removes impurities bound to the magnetizable cellulose derivatives while leaving the nucleic acids bound to the magnetizable cellulose derivatives.

26. The method of claim 25, wherein the nucleic acids bound to the magnetizable cellulose derivatives are DNA and are eluted with an elution buffer, wherein the elution buffer releases the DNA bound to the magnetizable cellulose derivatives.

27. The method of claim 26, wherein the DNA released by the elution buffer is isolated.

28. The method of claim 23, wherein the polyethylene glycol has an average molecular weight of about 8000, and wherein the salt is sodium chloride.

29. The method of claim 28, wherein the concentration of polyethylene glycol is about 10%, and the salt concentration is between 0.25 M to 5.0 M.

30. The method of claim 23, wherein the nucleic acids and non-nucleic acid materials are obtained from a cell lysate.

31. The method of claim 30, wherein the lysate is prepared from cells of human, animal, plant, viral or bacterial origin.

* * * * *